United States Patent [19]
Ponstingl et al.

[11] Patent Number: 4,637,730
[45] Date of Patent: Jan. 20, 1987

[54] OPTICAL AND ELECTRONICALLY COMPARED ABSORPTIOMETER

[75] Inventors: Michael J. Ponstingl, Jefferson County; Walter N. Trump; Robert C. Kessler, both of St. Louis County, all of Mo.

[73] Assignee: Custom Sample Systems, Inc., St. Louis, Mo.

[21] Appl. No.: 651,802

[22] Filed: Sep. 18, 1984

[51] Int. Cl.⁴ .................. G01N 21/85; G01N 21/31
[52] U.S. Cl. .................. 356/411; 250/565; 356/435
[58] Field of Search .............. 356/435, 411, 414; 250/565

[56] References Cited

U.S. PATENT DOCUMENTS

| | | | |
|---|---|---|---|
| 2,273,356 | 2/1942 | Holven et al. | 356/435 |
| 3,489,906 | 1/1970 | Beer | 356/435 |
| 3,822,097 | 7/1974 | Allington | 356/435 |
| 3,838,925 | 10/1974 | Marks | 356/435 |
| 4,152,075 | 5/1979 | Rellstab et al. | 356/435 |
| 4,273,449 | 6/1981 | Schmid | 356/411 |

Primary Examiner—Vincent P. McGraw
Attorney, Agent, or Firm—Paul M. Denk

[57] ABSTRACT

This invention relates to an optical absorptiometer which is characterized by a light source unit of a broad wavelength having a source of constant energy which is collimated into two light beams, one of which is transmitted through the liquid to be measured, and another beam which is transmitted through a conductor and acts as a reference beam, and a detector unit which contains two photocells, one photocell for measuring the beam transmitted through the liquid to be measured, and another photocell which measures the reference beam, a position in the absorptiometer for optically placing the liquid to be measured between the source unit and the detector unit, and means for measuring the energy difference between the light beams of the measured liquid and the reference beams in terms of absorbance, and means for converting this result to an electrical signal. In the preferred embodiment, the constant energy in the light source is controlled by feedback circuitry; the reference beam is transported by a fiber optic cable to the reference photocell of the detector unit; water condensation on the optical and viewing windows is prevented by means of dry air flow; the electrical signal is displayed and/or relayed to control an operation; and the reference beam is a segment of the original light beam from the source.

5 Claims, 9 Drawing Figures

OPTICAL AND ELECTRONICALLY COMPARED ABSORPTIOMETER

BACKGROUND OF THE INVENTION

This invention relates to an optical absorptiometer for measuring light absorption of a liquid.

Heretofore optical absorptiometers have been available for measuring light absorption of a liquid. However, these absorption meters employ a broad band of an unconstant light source. In addition, they do not employ a true reference light with which to compare the beam absorbed by the liquid to be measured. As a result, they do not give truly accurate results. We have now devised an optical absorptiometer which employs light of a broadly controlled wave length of a constant source and comparing it with a true reference wave length. Thus resulting in more accurate results.

SUMMARY OF THE INVENTION

This invention concerns the processing of a controlled light beam source of constant energy and obtaining two beams from said light source, one beam passing through the liquid to be measured and to the first photocell of the detector, and the second beam passing through a conductor and to the second photocell of the detector; means for measuring the energy difference between these light beams and converting this difference to a differential electrical signal. This signal can be employed in many laboratory process applications where color and/or turbidity indicate concentrations, impurities, the stage of the process reaction, etc., for example in the following areas:

I. Biotechnology:
  Bacterial/yeast/plant cell manufacturing.
II. Chemical:
  Soluble/insoluble product detector.
III. Petrochemical:
  Feed stocks/products clarity detection
IV. Food/Beverage:
  Product absorption specifications.

The electrical signal can be displyed and/or cause the performance of an operations means of a relay, such as stopping, modifying, changing, etc., a process and the like.

Distinctive features of the invention include the following:

1. The selection of a desired wave length of light energy perhaps of the desired narrow wave length by means of narrow band pass filters and detectors.

2. A true reference is achieved by separating and focusing the light energy employed by means of a collimating rod into a reference light and carrying this energy to one of two optically matched photocell detectors. The other photocell detector records the light absorption transmitted through to liquid sample itself.

3. The light source is controlled for constant energy by feedback circuitry.

4. Measurements by the absorptiometer can be made in both laboratory and process operation settings.

5. The absorptiometer can be adapted to measuring liquids in containers such as pipes of from about one and one-half to six inches path length.

6. The light measured by the aborptiometer can be converted to usable process control electrical signals.

7. The absorptiometer can be facily aligned optically on the process pipes.

8. Water condensation can be prevented from forming on the optical windows by any suitable means such as by dry air flow.

BRIEF DESCRIPTION OF THE DRAWINGS

The following Figures illustrate the invention.

DESCRIPTION OF THE PREFERRED EMBODIMENT

While the preferred embodiment of the invention has been set forth herein, it is not intended to limit the invention solely thereto, but to include all variations and modifications within the spirit of the invention.

The optical absorptiometer is a device for indicating, and controlling from, the optical absorption property of a liquid stream. The change which is measured may be the result of changes in either the color or the turbidity of the flowing stream. Applications of the optical absorptiometer include measurement of the concentration of a component in a stream, detection and measurement of contamination, and detection of the interface between two streams. The instrument displays digital absorbance, and produces a corresponding 4–20 mA current output, as an indicator. The absorbance span and zero of the current output are selectable. A relay output also is provided, with contract operation at a selected absorbance value, for the purpose of energizing an alarm or other indicator showing, as an example, a too turbid a conditioner.

The optical absorptiometer consists of two units: an optical unit, containing a light source and a detector, which mounts on a pipe line fitting having optical windows, each which may be twin windows allowing air circulation therebetween, and a wall-mounted display unit. The two units are connected by electrical cable. The source and detector components of the optical unit are connected electrically and also by an optical fiber cable, or other conductor.

Figure 1:
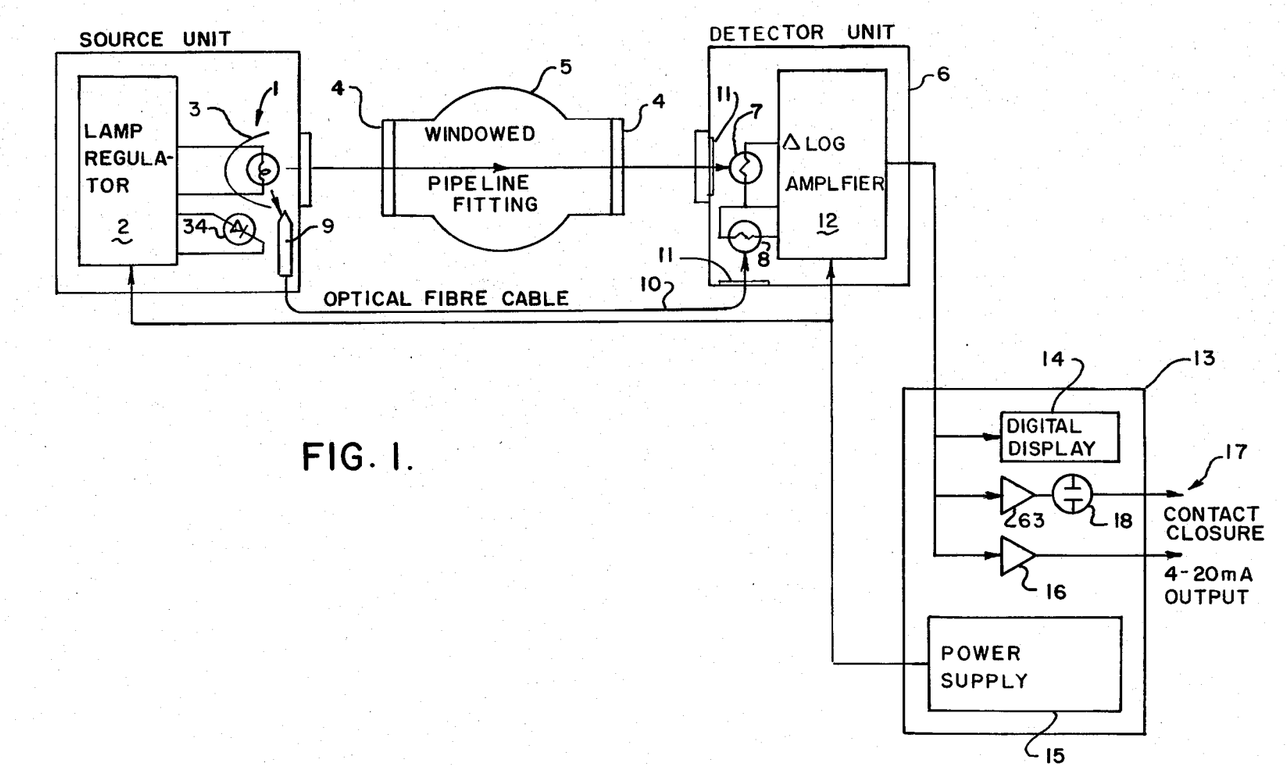
FIG. 1 shows a Functional Diagram.

FIG. 1 shows the functional components of the optical absorptiometer. The source unit contains a tungsten-halogen lamp 1 as the light source. The type of desired lamp may be a Philips No. 13165, obtained from Philips Co., of The Netherlands. This lamp is controlled for constant intensity of light output by means of optical feedback to an infrared-sensitive detector mounted behind the lamp, as at 2. The detector receives radiation transmitted through the dichroic reflector 3 of the lamp, while the visible light is reflected forward through the transparent windows 4 of the fitting 5 installed in the liquid pipe line. The detector unit 6 is mounted on the other side of the pipe line fitting, receiving the light transmitted through the liquid. The detector unit contains two photocells 7 and 8. These photocells may be of the type that can be obtained from Clairex Company of New York. The one photocell 7 is in the transmitted light beam. The other photocell 8 receives a small part of the light from the lamp 1 which is intercepted by a light pipe 9 and carried through an optical fiber cable 10, or other conductor, from the source unit to the detector unit. The light beams may be filtered by filters 11, in order to change the wavelength response characteristics of the instrument. A differential logarithmic amplifier 12 in the detector unit produces an electrical output signal which represents the negative logarithm of the ratio of the light intensity passing through the sample to that passing through the fiber optic cable. In the display unit 13 this signal is applied to a digital display 14 which reads the relative absorbance of the liquid in the pipe line. A 4–20 mA current output also is produced, proportional to the absorbance reading, and a solid-state relay contact closure occurs at a selectable value of absorbance. Also, a power supply 15 furnishes 120 volt power, and other voltage, for operations of the unit.

The display of the optical absorptiometer shows the value of absorbance, within a range of −3.99 to +3.99. Absorbance (formerly called optical density) is defined as $$A = \log_{10}(I/I_o)$$

where A is the value of absorbance, I is the light intensity at the measuring photocell and Io is the light intensity at the reference photocell. A zero control in the electronic circuit provides for setting the display to read 0.00 (or other desired value) when a reference stream is present in the pipe line. For colored solutions, the value of absorbance is usually closely proportional to the concentration of the colored constituent in the solution. For turbid suspensions the absorbance is usually not a linear function of the concentration of suspended solid, but absorbance still is a useful measure of solids concentration.

For a colored solution, the absorbance is related to the concentration of the colored material and the length of the light path through the solution by $$A = acl$$

where A is the absorbance produced by a solution which has a concentration C and a path length l. The constant "a" is a constant characteristic of the substance. If the concentration is in $kg/m^3$, and the path length in meters, constant "a" has the dimensions $m^2/kg$. Absorbence is dimensionless.

In the case of a suspended solid, the measured absorbance is not a linear function of the solids concentration. Typically the absorbance will increase almost linearly with solids content at low concentration, but will become almost independent of solids content at high concentration.

The following are typical specifications for an optical absorptiometer.

| 1. Optical specifications: | |
|---|---|
| Light source | Tungsten-halogen lamp |
| Detectors | Cadmium sulfide photo-conductive cells |
| Wavelength response | Peak 550 nm; 50% response points 505 and 675 nm |

Note: Filters, such as at 11, can be supplied to change the wavelength response characteristics of the instrument. Detectors of other response characteristics also are available.

| | |
|---|---|
| Absorbance display range | −3.99 to 3.99 |
| Range of zero adjustment | −3.99 to 3.99 |
| Absorbance reading with water in pipe and zero control centered. | −1 approx. |

| -continued | |
|---|---|
| 2. Electrical specifications: | |
| Power requirement | 100–140 volts, 60 Hz, 500 mA |
| Signal output | 4–20 mA |
| | As installed, 4 mA at reading .00; 20 mA at overflow from 3.99. Output 4 mA can be set by internal switch to any unit reading from −3.00 to 3.00; span 4–20 mA can be set by internal switch to 2,4, or 8 absorbance units. |
| Signal loop resistance | 0–600 ohms |
| Relay type | Solid-state |
| Relay operation mode | As installed, opens on increasing reading. Can be reversed by internal switch. |
| Relay set-point range | −3.99 to 3.99 |
| Relay hysteresis | 0.2 absorbance unit |
| Relay operation time delay | 1 second, approx. |
| Relay contact rating | 100–140 V, 2.5 A |
| 3. Mechanical specifications: | |
| Pipe fitting required | Perlick observer, nom. 1.5" to 6" pipe size, with hubs 110 mm (4.31") diameter. |
| Dimensions of optical assembly as installed on nominal 3" pipe line | 330 mm (13") long, 200 mm (8") high 255 mm (10") wide |
| Dimensions of display unit | 300 mm (12") wide, 200 mm (8") high, 170 mm (6.6") deep. |

As further can be noted from FIG. 1, the comparative signal derived from the log amplifier, that signal which is representative of the comparison made between the reference signal light passing through the cable 10, and that signal representative of the light passing through the sample, is generated as an output, as previously explained, of between 4 to 20 ma of current, after it passes through the amplifier 16. The contact closure, generally identified at 17, is a comparative amplifier used in conjunction with the relay and which can detect when a malfunction may be occurring in the processing of any fluid passing through the pipe line, and indicate the need for some attention and perhaps a shut down as a result thereof. For example, where the output signal from the log amplifier, or detector unit 6, is generally within a range of 4 to 20 ma of current, or at some level within that range, in the event that some problem is encountered with respect to the fluid passing through the pipeline, such that the amperage may be far less than 4 ma, or rise above 20 ma thereof, or if the ma amperage develops a readout that is lessor or greater than a predetermined quantity or level, as for example, greater or less than the 20 ma of current output, then the contact closure or its relay or switch 18 may be automatically shut off, and which may signal an alarm, or perhaps even shut off the flow of the fluids, as a result of that detection.

Figure 2:
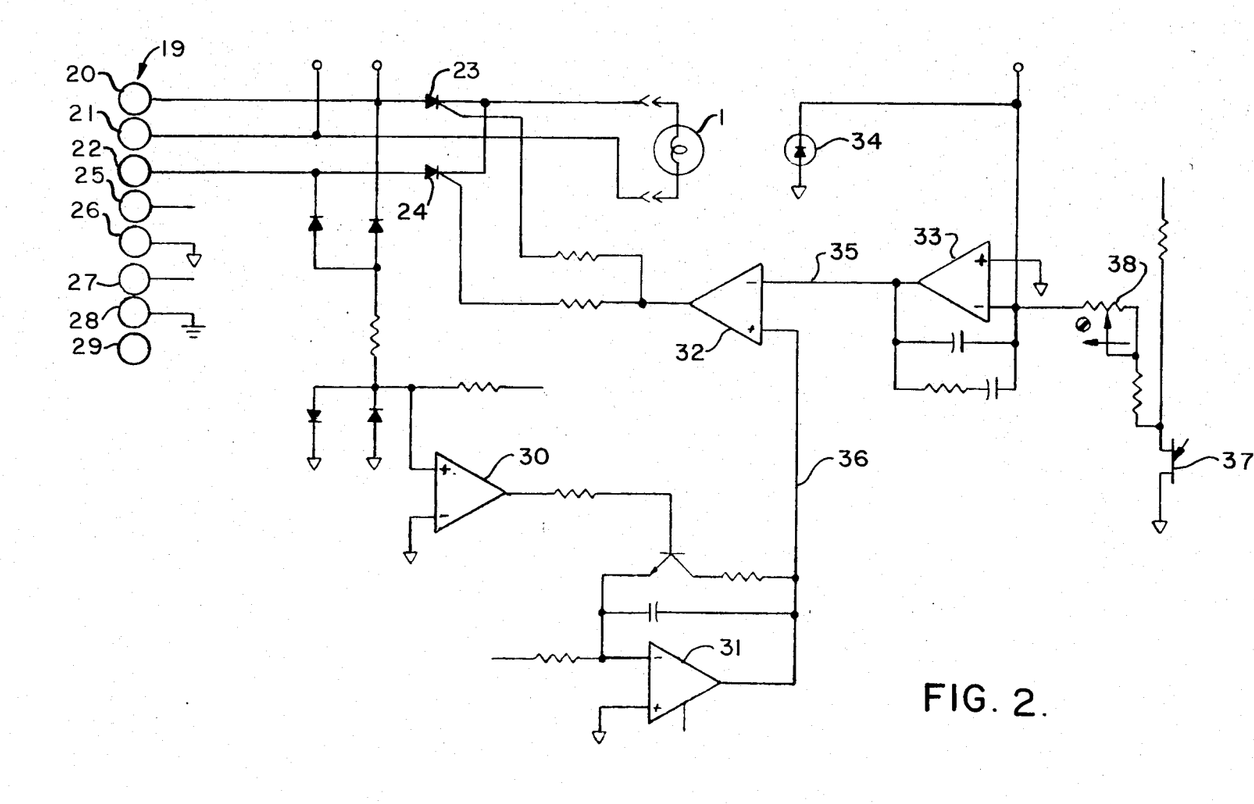
FIG. 2 shows a Source Unit Electronic Circuit.

FIG. 2, as previously described, shows the source unit electronic circuit, as of the type that is applied for application of the lamp regulator unit 2, to provide energization to the lamp source 1, and in addition, to provide for functioning of the pipe light 9, that taps a reference beam for transfer to the detection unit, and which functions as a reference light to the light with its absorbancy passing through the pipeline fitting 5.

As an example, provided along the left hand margin of this circuit diagram is disclosed the various electrical taps, as at 19, the top three of which, such as at 20 through 22, supply power, as from a power supply, for operations of the lamp 1 of the said source unit. The silicon controlled rectifiers (SCR)23 and 24 provided within the circuit lines 20 and 22, are set forth therein so as to regulate either more or less voltage to attain access to the lamp, for its energization, so that the lamp can be controlled for illumination at very precise or predetermined rms voltages. The next three contact points as at 25 through 27, provide operating voltages, as from the power supply, for functioning of the various amplifiers of the circuitry for this particular invention. The tap point 28 simply provides a circuit line to ground, as for example, for grounding of the chassis of the invention. The contact 29 is simply a spare contact point that may be available for usage, if necessary. For example, the connector 29 may provide a means for connection of the signal from the detector unit to and through the source unit, and on to the display unit 13, and which signal is that which is generated within the detector unit, as during the operations of this device. The amplifiers 30 through 32 are provided within the circuitry of the source unit system, and in conjunction with the amplifier 33, provides a feedback ac voltage for allowing a very precise regulation in the illumination of the lamp 1, during its functioning. For example, the photo diode 34, which is also disclosed in FIG. 1, picks up a portion of the light signal generated by the lamp 1, and provides for a phase change in the signal from said photo diode, as through operations of the amplifier 33, and its arrangement in parallel with the various capacitors, and resistances, as shown, then provides a signal that is out of phase with the signal originally detected by the element 34, and which signal is conducted through circuit line 35 and to the amplifier 32 where that signal is compared with the signal conducted through the circuit line 36, for providing for particular timed energization of the switches or rectifiers 23 and 24, in order to maintain a more precise and constant illumination of the lamp 1, and to assure that a proper light source is being emitted therefrom, and not one that effects a aberations or deviations in the light detections desired and required by the detector unit 6. Thus, it can generally be stated that the circuitry of FIG. 2 is simply provided for furnishing a precise regulation of the light emitted by the lamp 1. Also, to assure such, the unijunction transistor 37 compensates for temperature variations in the unit, and in addition, the potentiometer 38 provides for service setting of the lamp intensity as may be periodically required.

Figure 3:
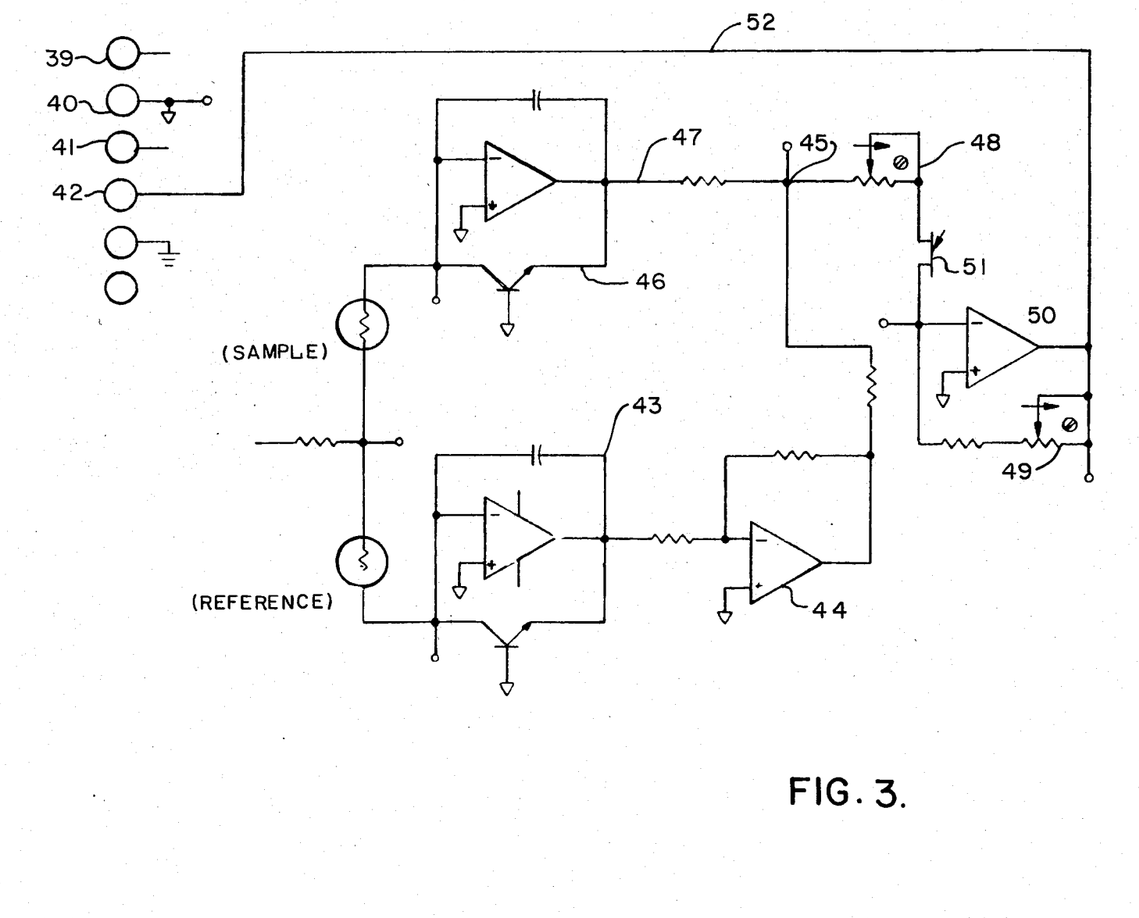
FIG. 3 shows a Detector Unit Electronic Circuit.

FIG. 3 discloses the circuitry for the detector unit 6, and it as can be noted, the three contact points 39 through 41 conduct the power supply voltages to the detector unit during its functioning. In addition, the contact point 42 is the output from the detector unit, although it is arranged internally of the unit 6. As can be seen, from the circuitry of FIG. 3, the reference light signal is detected by element 8, and which signal is then processed by the reference log amplifier 43, inverted by the inverter 44, and then conducted to a additive or summing point 45, within the circuitry. In addition, the detector 7, as previously explained, detects the light beam passing through the sample flowing within the pipe line fitting 5, and this particular light signal, as detected, is passed through a sample log amplifier 46, and yields a voltage output that is logrithmic proportional to the signal detected by the photocell 7, as aforesaid. This particular amplified signal is then conducted by way of the circuit line 47 to the said summing point 45, but since the voltage passing through the inverter 44 is just that, an inverted signal, that reference voltage is subtracted from the sample voltage, at this point 45, so as to generate a differential but amplified log signal representative of the difference between the beam detected by the sample photocell, and the reference photocell signal, as previously explained. A pair of potentiometers 48 and 49 are provided for controlling the gain of the summed signal, which passes through the amplifier 50, with the unijunction transistor 51 providing for temperature compensation, in addition to the adjustments that can be made through the said potentiometers 48 and 49, so as to provide a signal output that is very constant and undeviating with respect to the representative signals detected by the said photocells 7 and 8, even after sustained and prolonged periods of operation for the device. The amplified signal is provided to the circuit line 52, of contact 42, and which is representative of that summed signal, as previously explained, detected by the said photocells.

Figure 4:
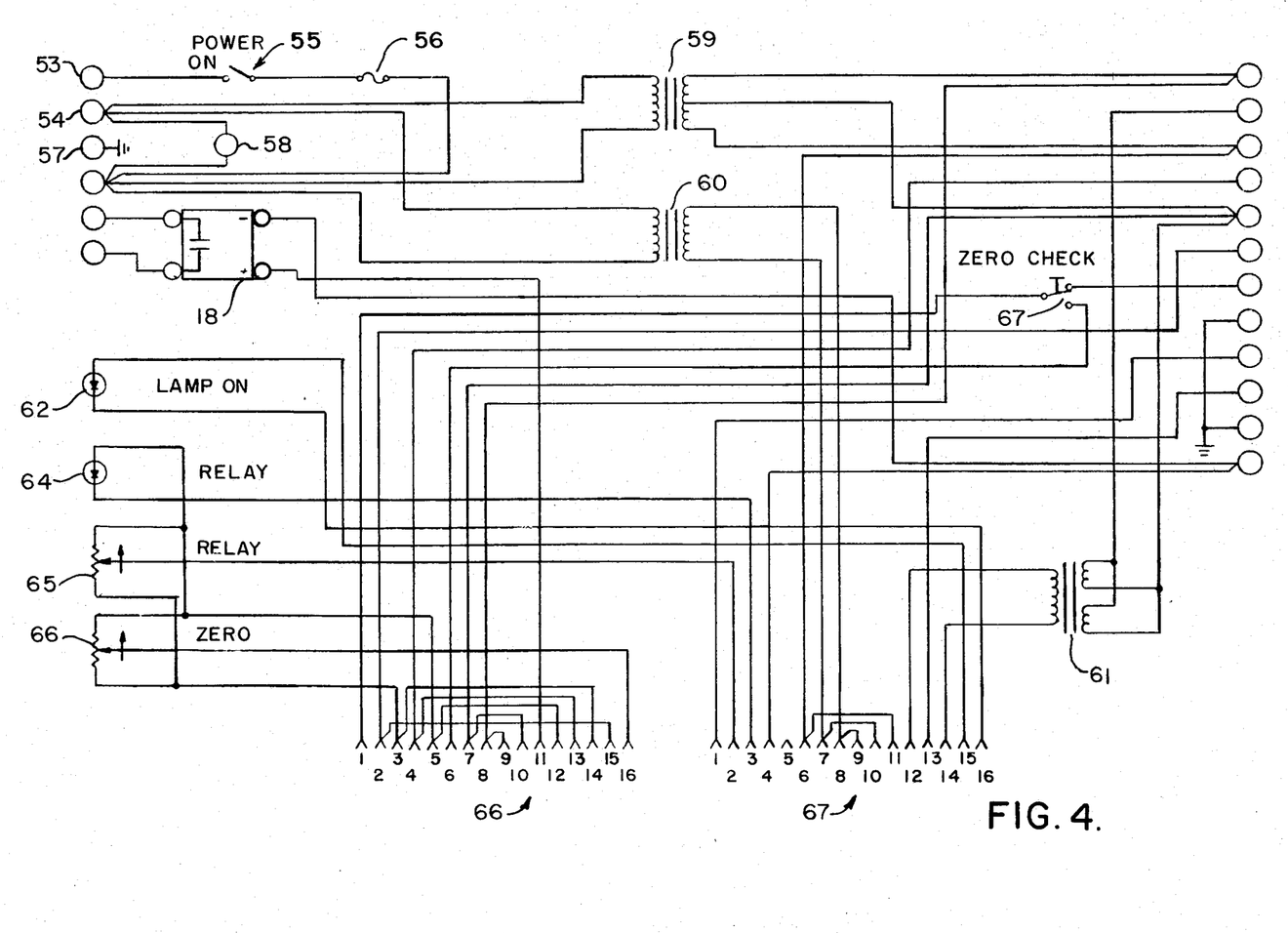
FIG. 4 shows a Display Unit Chassis Wiring.
Figure 5:
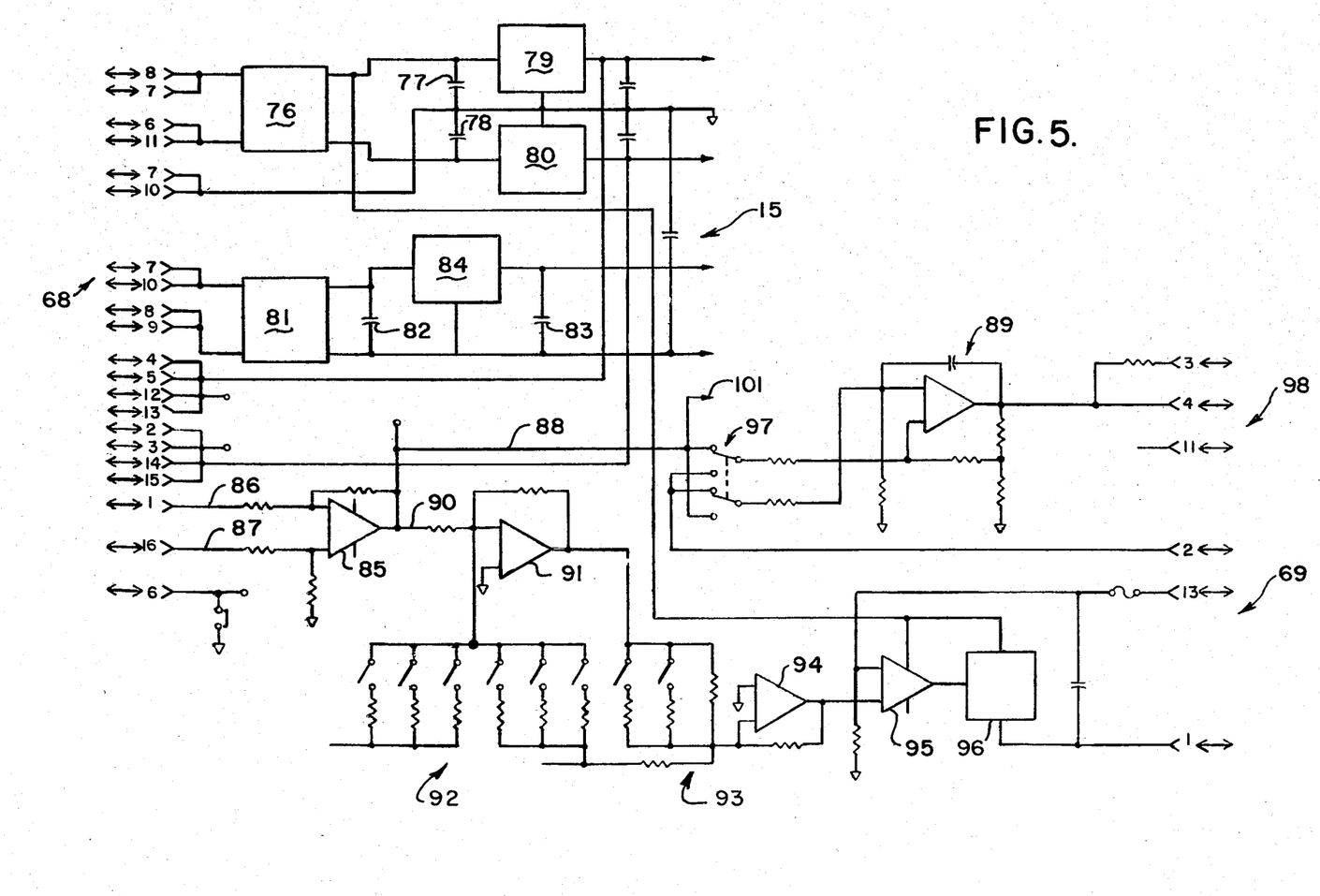
FIG. 5 shows a Display Unit Circuit Card (Power Supplies and Analog Circuits).

FIG. 4 discloses the circuitry provided in conjunction with the operations of the display unit 12, as previously generally identified. And, for that matter, it must be stated that the entire circuitry as disclosed also in FIGS. 5 through 7, are the circuit boards that are contained with the display unit 13, in addition, to FIG. 7 providing the circuitry for the digital display 14, contained within the said display unit.

FIG. 4 generally discloses the interconnect wiring for the contact points 53 and 54, that connect with the power supply. And, the switch 55, provides for the turning on or off of the unit. A fuse 56 is provided for protection, and the chassis is grounded as at 57. The indicator lamp 58 furnishes means for determining whether the unit is on or off. The two transformers 59 and 60 are step-down transformers, with the transformer 59 supplying power for operations of the source unit's lamp, and in addition, is connected with a portion of the power supply 15, contained within the display unit 13. The transformer 60 allows the conduct of charge to another portion of the power supply, as will be subsequently described. The transformer 61 is electrically connected for determining what use of current is made by the source lamp 1. This allows for an indication as to whether the lamp 1 is on or off. And, as can be seen, the lamp operating indicator 62, which is a light emitting diode, provides an indication of its functioning. In addition, the relay 18, as previously explained, takes the signal from the comparator amplifier 63, and provides for electrical connection with any alarm system, or shutoff switch, for purposes as have been previously defined. In addition, the LED 64 provides an indication as to when the relay 18 may be closed or opened, and is intended to provide an indication of some event occurs, such as a malfunction, or turbid liquid conditions within the pipeline, with respect to these type operations of the device, as previously explained. The adjustment potentiometer 65 is used for providing adjustment of the relay 18, so as to provide for a resetting as to when the relay will shut on or off, as desired. The potentiometer 66 provides for adjustment in the setting of the zero characteristic, or some other level or number, at which the digital display 14 is to display particular numbers. The zero check switch 67 allows for the digital display to receive a signal either from the detector unit, during the unit's functioning, or alternately, from the circuit board, as shown collectively in FIGS. 5 and 6.

Figure 6:
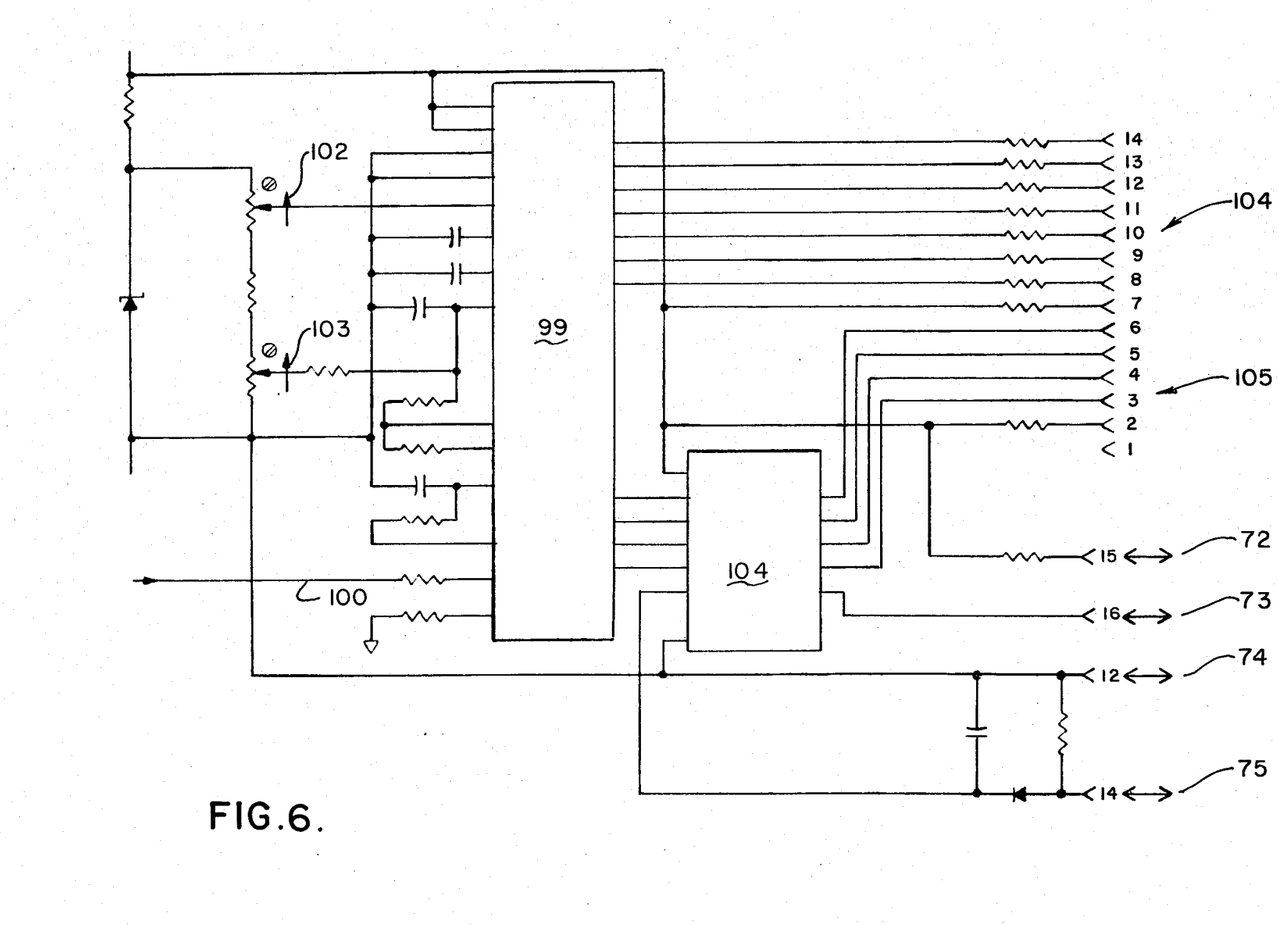
FIG. 6 shows a Display Unit Circuit Card (Integrated circuits and Display Driver).
Figure 7:
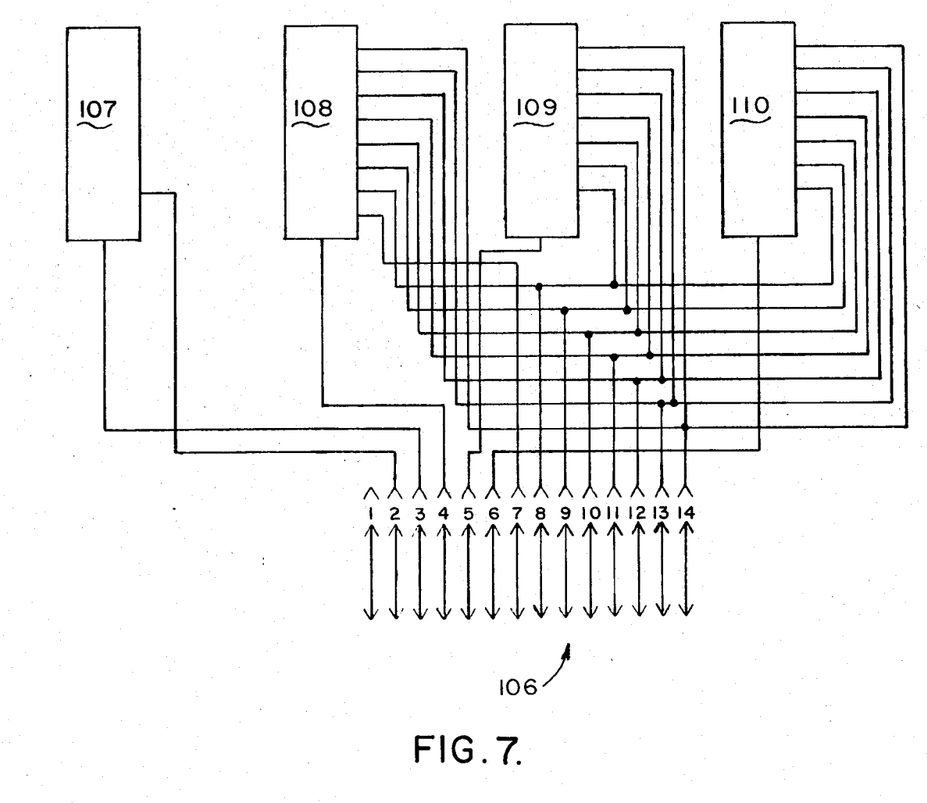
FIG. 7 shows as Display Unit Display Card.

With regard to the circuitry disclosed in FIG. 5, and which shows a display unit circuit card, that particular circuitry connects with the corresponding pin connectors, as at 68 and 69 of FIG. 4, with related connecting points 70, and 71, as provided in FIG. 5, in addition to the four connecting points 72 through 75, as shown in FIG. 6, and for purposes as will be subsequently described In referring, once again, to FIG. 5, the power supply 15 is generally disclosed, and the bridge rectifier 76 takes the step-down voltage from the transformer 59, rectifies it by means of the capacitors 77 and 78, and which voltage is then regulated to a plus or minus 5 volts, by means of the regulators 79 and 80. This output voltage then is provided for furnishing the operating voltage for use throughout the system of this device. The bridge rectifier 81 obtains voltage from the transformer 60, which signal is then filtered by the capacitors 82 and 83, regulated by the voltage regulator 84, with the output of the voltage from the regulator being approximately 5 volts. The amplifier 85 receives the voltage signals by way of circuit line 86 from the zero check switch 67, which has been previously explained. The amplifier 85 amplifies the two signals over the circuit line 86 and 87, and yields a voltage, which is the difference between the voltage from the zero potentiometer 66 and the zero check switch 67. This amplifier may be obtained from National Semiconductor as amplifier No. LF444CN. That signal then goes to two different locations, one, by way of the circuit line 88 to the relay comparator 89, and in addition, is conducted by way of the circuit line 90 to the amplifier 91, whose offset can be changed by the various switches, as at 92. In addition, these switches provide for a regulation in the amplification of the signal, through the amplifier 91, with its output passing through additional switches 93, and to the amplifier 94, with the switches 93 providing for gain changes in the amplifier 94. The output of the amplifier 94 passes through another amplifier 95, and the regulator 96, to provide an output of a signal that may vary between the range of 4 to 20 ma output. It might be commented that the amplifier 16, as previously explained in FIG. 1, is representative of the combination and operations of the amplifiers 94 and 95, in addition to the functioning of the regulator 96, so as to afford that desired amperage output, as noted. The switches 92 and 93 provide a regulation and setting of the ma output of the amplifier generally designated at 16.

The switch 97 provides for resetting or activation of the relay 18 on either an upward voltage, which is the signal that is being conducted from the detector unit 6, and this switch 97 determines and detects as to whether the relay 18 is to be activated depending upon an increase or perhaps a rapid or accentuated decrease in the signal being detected, with the signal then passing through the comparative amplifier 89(63) for conduct of voltage to the contact closure or relay 18, as previously explained. The outputs from the amplifier 89, as by way of the circuit lines 98, are for functioning of the relay 18, in addition to the relay indicator 64, and which provide for generation of an alarm or other signal indicating that excessive parameters during fluid flow have been encountered. The ouput voltage at 18 may vary between 0 to 5 volts.

FIG. 6, as previously explained, discloses another of the display unit circuit cards. Generally, this circuitry discloses an integrated circuit 99, and which generally functions to take the signal from the detector unit 6, to process it, and to provide a readout of digital signals to the display 14. This type of integrated circuit 99 may be of the type that can be obtained from National Semiconductor, located in Connecticut, and can be obtained as Model No. ADD3701CCN. The signal to the integrated circuit 99 is conducted by way of circuit line 100 from the amplifier 85, by way of the identified circuit line 88, and from the lead 101. The various circuitry, such as the variable potentiometers 102 and 103 provide a reference and feedback voltage, respectively, to provide for proper operations of such an integrated circuitry 99, as shown. This is standard in the art. Generally, the outputs, as by way of the circuit lines 104, collectively, provide a multiplexed output display, with decimal point, for disclosure upon the digital display 14, of the absorbance values of the fluid being subjected to the light during processing. It might be commented that these values may be read in terms of designated units, as previously explained in this application, with the absorbancy display range for this particular invention being set between $-3.99$ to $+3.99$, depending upon the setup for the application. It might be explained, by way of background information, that the absorbance of light by a solution provides a very definite range of indication of the amount of light absorbed by fluids, as is well known in the art of spectrophotometry, as previously explained in this application. The integrated circuitry 104, and which can be obtained from National Semiconductor, as Model No. 75492, functions to buffer the output of the integrated circuitry 99, to assure that the proper operation of said integrated circuit is achieved, and also has drive capabilities by way of its circuit lines 105 to provide enough current drive capabilities to properly operate the display unit 13.

The circuitry as at 74 and 75 function in cooperation with the transformer 61, to provide an indication as to when the lamp 1 may be functioning, by sensing the current draw of the lamp during its operation. And, the current herein is conducted from the integrated circuit 104 and through the circuit lines 72 and 76 for illuminating the LED 62, indicating when the lamp is on, as aforesaid.

FIG. 7 discloses the digital display unit 14, its circuit lines, and the unit connects by way of its contact points, as at 106, to the contacts 104 and 105, as previously explained, of the integrated circuit 99. Each of the four displays 107 through 110, of this display, are of the standard 7-segment type of common cathode LED display, as is so well known in the art. In this particular instance, for application in this particular apparatus, four displays are required, in order to give that reading between $-3.99$ to $+3.99$, as previously reviewed, with respect to providing means for displaying a value of absorbancy.

By way of example, and in referring to the circuit diagrams of this invention, in addition to the schematics of the invention as shown in FIG. 1, a routine operation of this optical and electronically compared absorptiometer, which generally is to provide an optical absorption means for comparing a supply light signal with a reference signal, as earlier explained, can generally be identified as follows. In referring to FIG. 1, in addition to FIG. 4, the power supply 15, as explained in FIG. 5, is initiated through the off-on switch 55, of FIG. 4. This provides the transmission of operating voltages throughout the system, but more specifically, to the lamp 1, in the manner as previously explained in FIG. 2. When this occurs, the lamp, which by now will be very precisely functioning to furnish a finely tuned light beam across the pipeline fitting 5, will provide for the detection of that particular signal by the photocell 7. But, at the same time, a portion of the light beam is picked up by the light pipe 9, conducts the beam of light by way of the fiber or other style cable 10, to the reference photocell 8. When a fluid is passing through the pipeline fitting 5, which might be fluid in the category of beer, or other liquid food product, during its processing, there more than likely will be a variation in the two light beams with some of the light being absorbed by the liquid product causing a differential between the light signal detected by the photocell 7, and that which is detected by the reference photocell 8. Then, through the functioning of the circuitry as previously explained in FIG. 3, there is obtained an output signal, as along the circuit line 52, which is the summation of these two generated signals, but in actuality, is a deduction of the reference voltage from the sample voltage processed therein. The signal as now conducted through the circuit line 52 passes into the circuitry of FIG. 5, over the circuit line 86, where it is conducted through the circuit line 101 to the integrated circuitry 99, where it is then further processed for display upon the digital display 14, upon the various digital display units 107 through 110. In addition, the voltage at circuit line 88 is, as previously explained, processed by the amplifier 89, compared with the voltage from the relay potentiometers 65, through the switch 97, to provide an output at 98 for operations of the relay 18, to provide for functioning of the contact closure, as previously explained. Furthermore, the signal at circuit line 90 is further processed by the amplifiers 91, 94, 95 and the regulator 96, for furnishing that milliamperage output, generally identified as by way of the amplifier circuitry 16, in FIG. 1. It might be commented, once again, that the amperage output at this juncture provides a means of indication, as for example, to the beverage processor, to determine exactly the quality of beverage being processed. As for example, if water simply is passing through the pipeline fitting 5, perhaps there is very little light differential between the sample and the reference photocell detections. Hence, very little amperage, or perhaps in the range of 4 ma or slightly greater ma may be detected. On the other hand, if the beverage being processed deviates, or is too colored or clouded, or perhaps becomes too opaque, as if too much of some ingredient causes too much turbidity in the pipe line, then the ma reading may become excessive, approaching in the range of 15 to 20 ma, which provides an immediate indication to the processor that some correction is immediately needed.

The following illustrates the installation of the preferred embodiment.

Installation

Mechanical Installation

Optical Assembly:

The optical assembly is designed for mounting on a Perlick observer fitting, of any nominal pipe size from 1.5" to 6". The nominal diameter of the window hubs of the fitting is 110 mm (4.31"). Before beginning installation, the optical assembly is checked to fit properly on the hubs of the observer fitting as installed.

One connects the purge air lines (not shown) to the purge fittings on each mounting plate or transparent window 4 of the optical assembly. The purge air pressure required is merely enough to produce a low dry air flow through the space between the observer fitting windows and the windows of the optical unit so as to prevent condensation on the observer fitting windows and the windows of the optical unit.

Display Unit:

The display unit 13 can be mounted on a wall or other vertical surface, as close as feasible to the optical assembly, and at a convenient height for reading the display and adjusting the controls.

Electrical installation

Figure 8A:
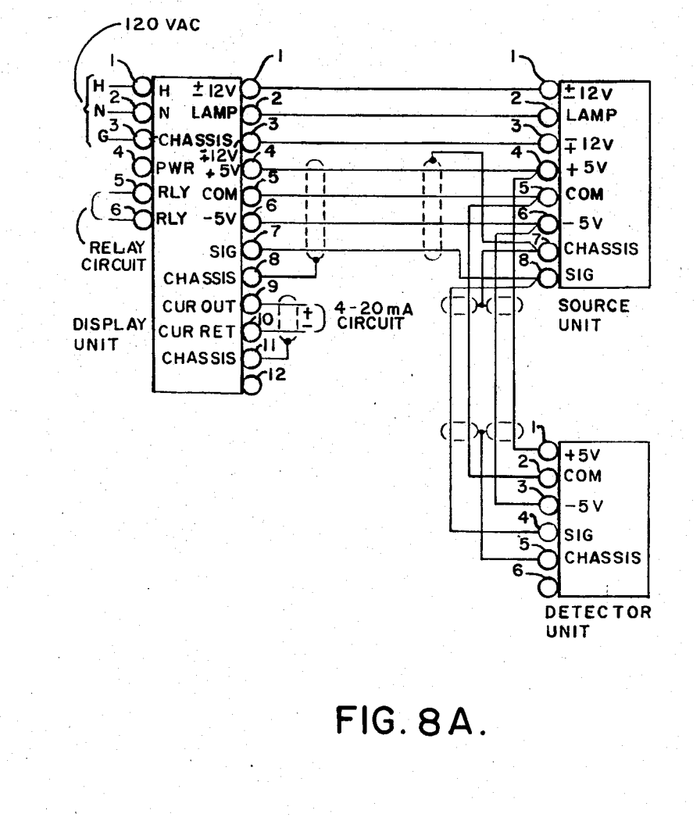
FIGS. 8A and 8B shows an Installation Wiring.
Figure 8B:
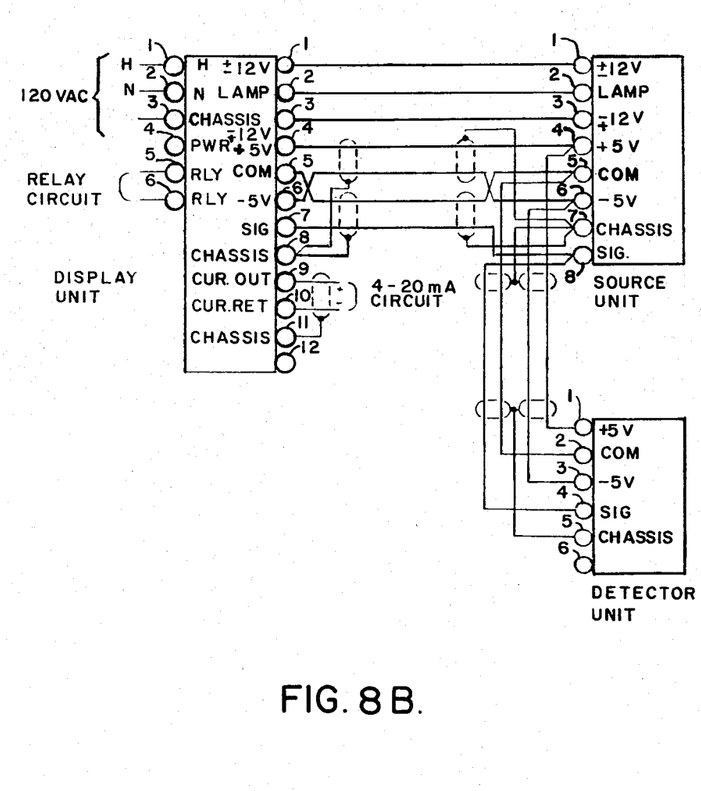

Optical assembly:

FIG. 8, shows the wiring required between the source and detector units of the optical assembly, and between the optical assembly and the display unit. A 3-conductor shielded cable joins the source and detector units; 4-conductor shielded and 3-conductor unshielded cables join the optical assembly with the display unit. The 3-conductor unshielded cable from the display unit to the source unit should be #18 gauge for runs up to 3 m (10 ft.); for longer runs it should be #16 gauge. (The source unit can be identified by the lamp in the center of the unit. The detector unit has at the center a white insulator.) The shielded cables may be #20 gauge.

Display Unit:

The wiring at the display unit is shown in FIG. 8. In addition to the cables from the optical assembly, connections for the 120 VAC power, for the 4-20 mA current loop, and for the relay circuit are required.

The 4-20 mA circuit is not grounded within the display unit, and therefore may be either grounded or floating externally. The external wiring should be shielded, to avoid interference pickup.

The relay is not supplied with power internally. It should be wired in series with the external circuit to be controlled, and should be protected by a fuse of not more than 2.5 A rating, preferably of fast-blowing characteristic. The relay will function only with alternating current supply.

The following illustrates the operation of the preferred embodiment.

Operation

Initial Set-Up:

The initial set-up procedure for the optical absorptiometer consists of adjusting the absorbance zero control to make the absorbance reading correct for the liquid in the pipe line, and of adjusting the relay control to trip at a selected absorbance. The exact procedure to be used depends upon whether or not the pipe line may contain a liquid which can be taken as a standard, for example, water as a standard of zero reading. If this is the case, the absorbance display can be made absolute. Otherwise the absorbance display will be arbitrary, although not less useful than the absolute display.

In all cases the reading of the absorbance display is relative, in the sense that the display shows the value of $-\log$ (intensity of sample beam/intensity of reference beam through the optical fiber). However, if the operation permits setting to zero with water, then the readings will be referred to water as a standard of zero absorbance and the instrument zero setting can be checked against water to detect any drifting. If water, or other standard for setting zero, is not available, the instrument zero control must be set for an arbitrary display reading. The instrument is provided with a switch which permits the zero setting to be displayed, so that a specific setting can be recovered without the need for changing the liquid in the pipe.

Setting zero with water in the pipe:

1. The operator adjusts the zero control of the instrument until the display reads 0.00 (or is just changing between −0.00 and 0.00).

2. The operator presses the zero check button. The display now reads a value which represents the electronic offset required to produce the zero reading. It is useful to make a note of this value. In the future the instrument can be checked by pressing the zero check button, noting the reading and if necessary adjusting the zero control to return to the original value.

Setting zero with process stream in the pipe:

1. The operator adjusts the zero control until the display reads the desired value for the process stream. Selection of this value depends on having some knowledge of the optical properties of the stream. For example, if the stream is very turbid, a suitable setting might be 3.00. If the stream is transparent but deeply colored, a setting of 1.00 mght be appropriate. If the stream is only light colored or slightly turbid, or both, a setting of perhaps 0.20 might do. The display reads negative as well as positive, so for the display alone there is no need to avoid negative readings. As the instrument is supplied, however, the 4–20 mA current output covers only the display range of 0.00 to 3.99. Thus, to make full use of the 4–20 mA output the zero control should be set so that the display readings are always positive. If the instrument is set up initially with values such as those given above, experience will show what changes are needed to keep the display readings within the desired range.

2. The operator presses the zero check button, and notes, and records, the resulting display reading. To check the zero setting in the future, press the zero check button and adjust the zero control if necessary to bring the reading back to the recorded value.

Setting relay trip point:

The relay can be set to trip at any point within the range of the display. As the instrument is supplied, the relay contact opens an increasing reading. The relay trip point can be set either by waiting for the stream composition to reach the condition at which tripping is desired, or by first obtaining a history of display reading as a function of stream properties and then selecting a suitable reading for the trip point.

Setting relay to stream value:

1. If the stream absorbance is decreasing: the relay was previously open and now is to close. One turns the relay control counter-clockwise until the relay indicator lamp goes off (if it was on), then turn the control closkwise until the lamp just comes on. There is a time delay of about one second in the relay operation, which should be allowed for in approaching the trip point. The relay now will close when the absorbance reading falls to the value present when this setting was made. It will open on rising absorbance at a reading 0.20 higher than this value.

2. If the stream absorbance is increasing: the relay was previously closed and now is to open. One turns the relay control clockwise until the relay indicator lamp goes on (if it was off), then turns the control counter-clockwise until the lamp just goes off. The relay now will open when the absorbance reading rises to the value at which this setting was made. It will close on falling absorbance at a reading 0.20 lower than this value.

Setting relay to selected display value:

As a result of experience with the instrument, it may be found that the relay should trip at a certain displayed absorbance value. The relay can be set to operate at this value, even though the reading of the process stream at the time is different from this. The setting is done by using the zero and zero check controls to change the display reading, and then to return to the original reading.

1. The operator presses the zero check button. Notes, and records, the resulting display reading.

2. The operator uses the zero control to bring the display reading to the desired value for the relay trip point.

3. The operator follows the procedures above for setting the relay control to stream value.

4. The operator presses the zero check button and adjusts the zero control to bring the display reading to the value recorded in Step 1.

If the stream composition is changing rapidly enough to make it difficult to set the relay by the procedure in steps 2 and 3, the same procedure may be followed by holding down the zero check button throughout the procedure. This gives a steady reading, independent of stream variations.

Having thus described the invention what is claimed and desired to be secured by Letters Patent is:

1. An optical absorptionmeter which is characterized by a light source unit of a broad wave length having a source of constant energy which is transmitted as two separate light beams, one of which is transmitted as a main light source beam through a flowing liquid or the like to be measured, and the other beam which is transmitted as a reference beam, said reference beam being tapped from the main light source beam, a power supply for said light source, silicon controlled rectifiers operatively associated with said power source and light source to finely regulate the lamp voltage, said constant energy of the light source being controlled by feed back circuitry, a detector unit which contains two photocells, a position means in the absorptionmeter for optically placing the liquid to be measured between the source unit and one of its photocells and the detector unit, one photocell for measuring the light transmitted through the liquid to be measured, and another photocell which measures the reference beam, a log amplifier electronically connected with the liquid measured photocell and yielding a voltage output logarithm proportional to the signal detected by said photocell, a second log amplifier electronically connected with the reference light detecting photocell and yielding a voltage output logarithm proportional to the reference signal detected by the said photocell which measures the reference beam and the inverter electrically connected with the said latter amplifier and inverting the detected and amplified reference detected voltage, means for measuring the energy difference between the light beams of the measured liquid and reference beam in terms of absorbance, said means comprising a summing point provided within the circuitry of the detector unit and furnishing a voltage detection equal to the difference between the reference and liquid measured yielded voltages, and means for converting this energy difference to an electrical signal for display and control, integrated circuit means electrically connected to said detector unit and capable of receiving said signal therefrom, providing a processing of the said signal and furnishing a readout of digital signals, and a digital display unit coupled to said integrated circuit means and capable of receiving said digital signals and displaying the same, said digital display incorporating a LED display for visually displaying said processed signals.

2. The absorptiometer of claim 1 where the reference beam is transported through fiber optic cable to the reference photocell of the detector unit.

3. The absorption meter of claim 1 and including an optical and viewing means operatively associated with the position means for the liquid to be measured within the absorptionmeter, and air circulating means operatively associated therewith to prevent water condensation on the optical and viewing means through the passage of dry air therethrough.

4. The absorptiometer of claim 1 where the electrical signal is displayed and/or relayed to control an operation.

5. The invention of claim 1 and including filter means disposed for filtering the light beam after passage through the liquid and then for filtering the reference beam before detection by the photocells.

* * * * *